United States Patent [19]

Huizing et al.

[11] Patent Number: 4,949,367

[45] Date of Patent: Aug. 14, 1990

[54] X-RAY SPECTROMETER HAVING A DOUBLY CURVED CRYSTAL

[75] Inventors: Albert Huizing; Cornelis P. G. M. Zegers; Teunis J. A. Heijmans, all of Eindhoven; Maurits W. Van Tol, Almelo, all of Netherlands

[73] Assignee: U.S. Philips Corporation, New York, N.Y.

[21] Appl. No.: 330,242

[22] Filed: Mar. 29, 1989

[30] Foreign Application Priority Data

Apr. 20, 1988 [NL] Netherlands ............................ 881019

[51] Int. Cl.$^5$ .............................................. G21K 1/06
[52] U.S. Cl. ........................................... 378/84; 378/82
[58] Field of Search ............................ 378/71, 82–85, 378/49

[56] References Cited

U.S. PATENT DOCUMENTS

| | | | |
|---|---|---|---|
| 2,853,617 | 9/1958 | Berreman | 378/84 |
| 3,439,163 | 4/1969 | De Jongh | 378/84 |
| 4,351,063 | 9/1982 | Dineen et al. | 378/84 |
| 4,525,853 | 6/1985 | Keem et al. | 378/83 |
| 4,562,585 | 12/1985 | Göbel et al. | 378/83 |
| 4,649,557 | 3/1987 | Hornstra et al. | 378/84 |
| 4,780,899 | 10/1988 | Adema et al. | 378/82 |
| 4,807,268 | 2/1989 | Wittry | 378/82 |

FOREIGN PATENT DOCUMENTS 2579752  10/1986  France ................................. 378/84

OTHER PUBLICATIONS

"Concept and Design Procedure for Cylindrical Element Monochromators . . . ", by Chem Nuclear Instruments and Methods in Physics Research (1987), pp. 595–604.

Primary Examiner—Janice A. Howell
Assistant Examiner—John C. Freeman
Attorney, Agent, or Firm—Paul R. Miller

[57] ABSTRACT

An X-ray analysis crystal is also curved in a direction transverse to the dispersion direction to increase the radiation efficiency. As a result of this radiation diffracted at the crystal is focused towards a detector input. In order to ensure a non-deformable crystal surface the crystal is preferably bonded to a carrier having an adapted bonding profile.

11 Claims, 1 Drawing Sheet

X-RAY SPECTROMETER HAVING A DOUBLY CURVED CRYSTAL

The invention relates to an X-ray analysis apparatus comprising an X-ray source, a monochromator crystal curved in a dispersing direction elliptically or logarithmically, an object holder and an X-ray detector and to a monochromator crystal for such an apparatus.

A crystal for such an apparatus is disclosed in British patent specification GB No. 1,089,714 in which a method for the formation of such a crystal is also described. A further description of such an apparatus is given in U.S. Pat. No. 4,351,063 in which the crystal is mounted so that it can also be measured in transmission.

When such monochromator crystals are used in X-ray analysis apparatuses the drawbacks occur that on the one hand, the apparatus operates comparatively inefficiently as regards to radiation and that on the one hand, deviations in the desired crystal shape often occur. Both drawbacks adversely influence the measuring accuracy of the apparatus.

It is the object of the invention to avoid these drawbacks and for that purpose an X-ray analysis apparatus of the type mentioned in the opening paragraph is characterized according to the invention in that the monochromator crystal is also curved in a direction transverse to the dispersing direction.

Since the monochromator crystal in an X-ray analysis apparatus according to the invention is also bent in a direction transverse to the dispersing direction, hereinafter termed the sagittal direction, the X-ray beam, measured in this direction, is focused on a detector input so that a significantly better radiation efficiency is achieved.

In a preferred embodiment the crystal is curved circular-cylindrically in which the radius of curvature may be equal over the whole crystal but may also show a variation in the dispersing direction. A constant radius of curvature is simplest for crystal production while the radiation efficiency can still be improved with a varying radius of curvature adapted to the apparatus.

In a further preferred embodiment the crystal consists of, for example, a plane-parallel crystal, for example, of Si or Ge, bonded on a preformed carrier. The crystal may be bonded to the carrier, for example, by means of a polythene film or by means of UV-curing adhesive. The uniform pressure on the crystal required for the bonding can be realized by means of a double diaphragm method. Depending on the material of the carrier the profile may be provided in the carrier by means of milling, grinding or pressing.

A few preferred embodiments according to the invention will now be described in greater detail with reference to the accompanying drawing, in which.

Figure 1:
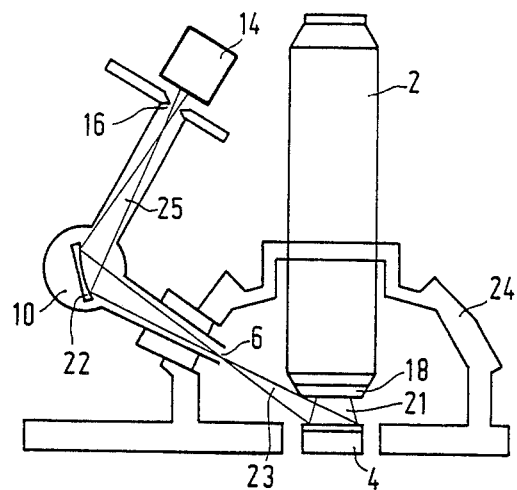
FIG. 1 shows diagrammatically an X-ray spectrometer according to the invention.

An X-ray spectrometer as shown in FIG. 1 comprises an X-ray source 2, an object table 4, an input gap 6, a crystal holder 10, a detection system 12 with a detector 14, detector or output gap 16. An X-ray filter 18 with which a wavelength track of the X-ray beam can be selected is incorporated between the X-ray source 2 and the object table 4. The X-ray source 2 is incorporated in a carrier 24 in which, for example, the input gap 6, the crystal support 10 and the output gap 16 are also mounted. An object 20 to be examined is placed on the object table 4 and is radiated by an X-ray beam 21 to be emitted by the X-ray source 2. X-ray beam 23 diffracted at the object impinges on an analysis crystal 22 via the input gap 6. An X-ray beam 25 diffracted at the analysis crystal 22 is then detected in the detector 14. A simultaneous spectrometer as shown is equipped with several input gaps, output gaps, detectors and crystal supports each of which is adapted to a wavelength to be adapted and hence to an element to be analyzed. The analysis crystal 22 directs radiation of a selected wavelength towards the detection system.

Figures 2, 3:
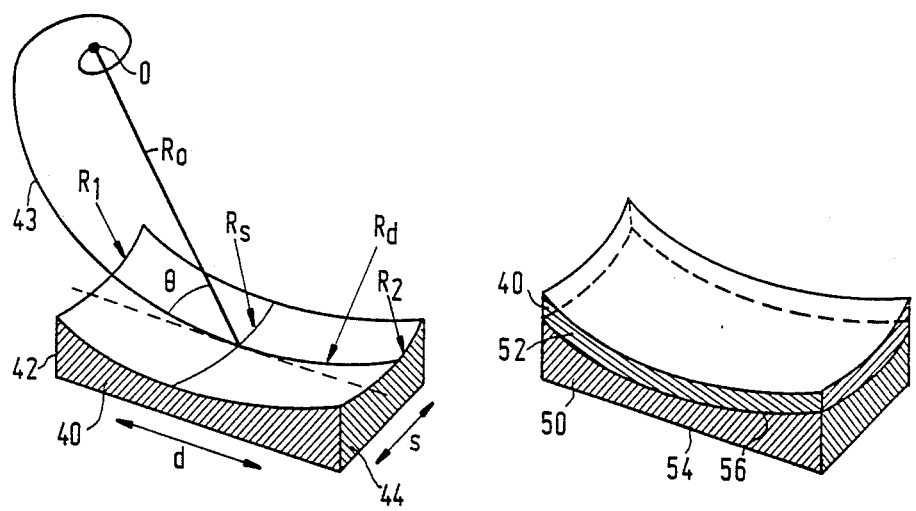
FIG. 2 shows diagrammatically a crystal therefor.
FIG. 3 shows an assembly of a crystal and a support.

An example of a crystal for such an apparatus is shown in FIG. 2. A wafer of crystal material 40, for example, of silicon or germanium cut along crystal faces to be sued for diffraction shows herein a dispersion direction d, a logarithmic curvature having a radius of curvature $R_1$ which is given by a logarithmic spiral 43 with center O. Radiation originating from the center O impinges on the crystal with a logarithmic curved crystal along the full cross-section of the crystal at the same angle $\theta$. According to the invention the crystal surface shows a curvature $R_s$ in a sagittal direction s which curvature may be equal throughout the crystal but may also vary from a beam $R_1$ on one side 42 of the crystal to a value $R_2$ on an oppositely located side 44 of the crystal. The radius of curvature varies, for example, in such a manner that the geometrical points of the centers of curvature also form again a logarithmic spiral with the same center. In particular $R_o$ is, for example, approximately 250 mm, the angle 74 is approximately 70° and $R_s$ is approximately equal to 260 mm. The crystal may also be curved in the dispersion direction according to a different curve, for example spherically as described in U.S. Pat. No. 4,649,557. As a result of the double curvature of the crystal, radiation in the sagittal direction is focused towards a detector device as result of which a significant gain in radiation efficiency is obtained. Also for example, the wafer of crystal material 40 may be of InSb, LiF, or pentaerithritol.

In an embodiment shown in FIG. 3 a crystal 40 is bonded to a carrier 50 in one side 52 of which a profile of the desired doubly curved shape has been provided. The carrier consists, for example, of aluminium in which the profile has been provided, for example by means of a numerically controlled milling machine and the crystal has been provided thereon by adhering, for example, with the interposition of a polythene film 56. For pressing the crystal for bonding purposes use may be made of a double diaphragm pressure method as described in British patent specification GB No. 727,077.

The carrier may also consist of material which is transparent to radiation with which an adapted type of adhesive can be cured, for example, UV-radiation. Bonding may then be carried out by radiating the adhesive from one side 54 through the carrier. A good example therefor is a vitreous carrier which is sufficiently transparent to UV-radiation to be able to cure an UV-curing layer of adhesive between crystal and carrier. When such types of adhesive are used an extremely thin layer of adhesive may be provided and curing can be carried out very rapidly. The bonding surfaces of carrier and crystal must show a great smoothness. When a polythene film is used for the bonding a less high smoothness may be used because the thickness of the film, for example 20 $\mu$m, compensates for unevennesses.

Polythene films having a good homogeneous thickness are readily available nowadays.

We claim:

1. In an X-ray analysis apparatus comprising an X-ray source, a monochromator crystal curved in a dispersing direction in one of an elliptical shape and a first logarithmic spiral of curvature, an object holder; and an X-ray detector, the improvement comprising said monochromator being curved in a sagittal direction transverse to said dispensing direction, the curvature in said sagittal direction being circular with a varying radius of curvature measured in said dispersing direction.

2. An X-ray analysis apparatus according to claim 1, wherein said curvature in said sagittal direction is defined by a curvature center located at a geometrical point, said geometrical point lying on a second logarithmic spiral, said second logarithmic spiral having a center coinciding with a center of the first spiral of curvature in said dispersing direction.

3. An X-ray analysis apparatus according to claim 2, wherein said monochromator crystal is bonded to a preformed carrier.

4. An X-ray analysis apparatus according to claim 3, wherein said monochromator crystal is bonded to said preformed carrier by a polyethene film.

5. An X-ray analysis apparatus according to claim 3, wherein said monochromator crystal is bonded to said preformed carrier by a UV-curing adhesive.

6. An X-ray analysis apparatus according to claim 3, wherein said monochromator crystal includes a crystal of one of Ge, Si, InSb, LiF and pentaerithritol.

7. An X-ray analysis apparatus according to claim 1, wherein said monochromator crystal is bonded to a preformed carrier.

8. An X-ray analysis apparatus according to claim 7, wherein said monochromator crystal is bonded to said preformed carrier by a polyethene film.

9. An X-ray analysis apparatus according to claim 7, wherein said monochromator crystal is bonded to said preformed carrier by a UV-curing adhesive.

10. An X-ray analysis apparatus according to claim 2, wherein said monochromator crystal includes a crystal of one of Ge, Si, InSb, LiF and pentaerithritol.

11. An X-ray analysis apparatus according to claim 1, wherein said monochromator crystal includes a crystal of one of Ge, Si, InSb, LiF and pentaerithritol.

* * * * *